(12) United States Patent
Colston et al.

(10) Patent No.: US 8,116,995 B2
(45) Date of Patent: Feb. 14, 2012

(54) MEDIA CHARACTERIZATION (75) Inventors: Scott L. Colston, Dundee (GB); Barrie Clark, Dundee (GB)

(73) Assignee: NCR Corporation, Duluth, GA (US)

( * ) Notice: Subject to any disclaimer, the term of this patent is extended or adjusted under 35 U.S.C. 154(b) by 490 days.

(21) Appl. No.: 12/004,398

(22) Filed: Dec. 20, 2007

(65) Prior Publication Data

US 2009/0164156 A1   Jun. 25, 2009

(51) Int. Cl.
*G01R 15/00* (2006.01)
(52) U.S. Cl. ............................. 702/57; 702/104; 702/189
(58) Field of Classification Search .................. 257/60; 324/663, 649, 675, 690; 327/4, 5, 90, 110, 327/111; 333/17.3, 19; 702/64, 104, 189, 702/57; 902/4, 22
See application file for complete search history.

(56) References Cited

U.S. PATENT DOCUMENTS

| | | | |
|---|---|---|---|
| 3,253,224 A * | 5/1966 | Smith et al. .................... 235/449 |
| 5,308,992 A * | 5/1994 | Crane et al. .................... 250/556 |
| 6,051,422 A * | 4/2000 | Kovacs et al. ................ 435/287.1 |
| 6,361,043 B1 * | 3/2002 | Hutchison ....................... 271/263 |
| 6,454,163 B2 * | 9/2002 | Peebles et al. ................. 235/379 |
| 6,647,133 B1 * | 11/2003 | Morita et al. .................. 382/124 |
| 7,128,259 B2 * | 10/2006 | Clark ............................. 235/379 |
| 7,341,179 B2 * | 3/2008 | Tocher et al. ................. 235/379 |
| 7,359,543 B2 * | 4/2008 | Tsuji et al. ..................... 382/137 |
| 7,427,376 B2 * | 9/2008 | Nagai et al. ................... 422/68.1 |
| 2010/0100146 A1 * | 4/2010 | Blomqvist ...................... 607/17 |

\* cited by examiner

*Primary Examiner* — Michael Nghiem
*Assistant Examiner* — Elias Desta
(74) *Attorney, Agent, or Firm* — Michael Chan (57) ABSTRACT

Methods and apparatus for media characterization in a self-service terminal are described. The media us characterized in the self-service terminal by passing it by two electrodes and measuring the impedance across those two electrodes. The media is characterized by analyzing the measured impedance. The impedance may be measured by applying a modulated reference signal to one electrode and detecting the current on the second electrode. In an embodiment, the detected current may be converted into a voltage signal and mixed with a phase shifted version of the modulated reference signal.

13 Claims, 11 Drawing Sheets

MEDIA CHARACTERIZATION

TECHNICAL FIELD

The present invention relates to media characterization in a self-service terminal. It is particularly related to, but in no way limited to, detection of the numbers of elements of media which have been picked from a media cassette in a self-service terminal (SST) such as an automated teller machine (ATM).

BACKGROUND

When dispensing media from a self-service terminal, such as bank notes from an ATM, it is very important that the correct amount of media (e.g. the correct amount of money) is dispensed. The media is stored in the SST in cassettes from which it is picked, one piece of media at a time, by a pick mechanism. Occasionally, the pick mechanism may accidentally remove more than one item of media from a cassette in a single pick operation and it is important that this is detected before it is dispensed as otherwise it would result in the user of the SST being dispensed more media than intended and than has been recorded. SSTs therefore include sensors which can detect double picks (i.e. where two pieces of media have been picked together in a single pick operation) and when a double pick is detected, the stack of two pieces of media is rejected (i.e. placed into a purge or reject bin) or recycled, if the SST has recycling capability.

Figure 1:
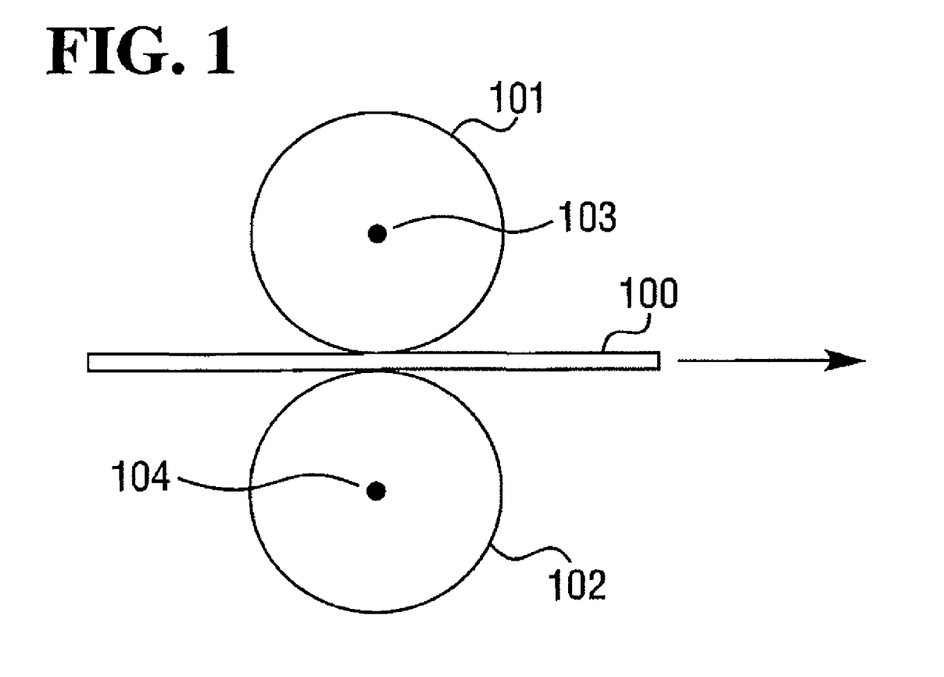
FIG. 1 is a schematic diagram of a typical media sensor in an SST.

A typical sensor which is used to detect double picks involves passing the media 100 between two rollers 101, 102 and detecting the resultant displacement of the axle 103 of one roller with respect to the axle 104 of the other roller, as shown in the schematic diagram of FIG. 1. The position of one of the rollers (e.g. roller 102) may be fixed. The axle displacement may be measured using a linear variable differential transformer (LVDT). An LVDT comprises three coils: a primary coil and two secondary coils, and the transfer of current between the primary and secondary coils is determined by the position of a magnetic core. At a centre position, the secondary voltages are equal, but if the magnetic core moves away from this centre position, one secondary voltage will increase and the other will decrease and therefore by monitoring these secondary voltages (or the difference between them), displacement can be detected. Instead of using a LVDT to detect the relative displacement of the rollers, the displacement may be detected using a strain gauge.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Methods and apparatus for media characterization in a self-service terminal are described. The media is characterized in the self-service terminal by passing it by two electrodes and measuring the impedance across those two electrodes. The media is characterized by analyzing the measured impedance. The impedance may be measured by applying a modulated reference signal to one electrode and detecting the current on the second electrode. In an embodiment, the detected current may be converted into a voltage signal and mixed with a phase shifted version of the modulated reference signal.

A first aspect provides a method of detecting media in a self-service terminal comprising: passing an item of media across a first and a second electrode; measuring an impedance across the first and second electrodes; and analyzing the measured impedance to detect the item of media.

As used herein, an "item of media" refers to media picked in a single operation. The item of media may comprise multiple individual entities (for example, multiple sheets) that are picked and transported together as a single item, or only a single entity (for example, a single sheet) that is picked and transported. Whether an item of media comprises one or multiple individual entities is only known when an item of media has been correctly characterized.

Measuring the impedance may comprise: stimulating the first electrode with a reference modulated voltage signal; and measuring a current from the second electrode.

As is known to those of skill in the art, impedance refers to the combination of a frequency invariant component (resistance) and a frequency-dependent component (reactance).

Measuring a current from the second electrode may comprise: converting the current from the second electrode into a varying voltage signal; and mixing the varying voltage signal with a phase shifted version of the reference modulated voltage signal to create an output voltage signal; and wherein analyzing the measured impedance to detect the item of media may comprise: analyzing the output voltage signal.

The measured impedance may comprise a small or negligible resistance and a reactance.

Analyzing the measured impedance to detect the item of media may comprise: analyzing the measured impedance to determine a quantity of media items in the item of is media.

Analyzing the measured impedance to determine a quantity of media items in the item of media may comprise: comparing the measured impedance to a stored value; and determining the quantity based on the comparison.

The item of media may comprise a document in sheet form, such as a bank note, a cheque, a ticket, a book of stamps, or the like.

The self-service terminal may comprise an automated teller machine (ATM), an information kiosk, a financial services center, a bill payment kiosk, a lottery kiosk, a postal services machine, a check-in and/or a check-out terminals such as those used in the hotel, car rental, and airline industries, a retail self-checkout terminal, a vending machine, and the like.

A second aspect provides a computer program comprising computer program code means adapted to perform all the steps of any of the methods described above when said program is run on a computer.

The computer program may be embodied on a tangible computer readable medium.

A third aspect provides a sensing mechanism in a self-service terminal comprising: a first and a second electrode; a reference signal supply connected to the first electrode, wherein the reference signal comprises a modulated signal; and an impedance measuring circuit connected to the second electrode for measuring an impedance of media passing the electrodes.

The first and the second electrodes may be substantially parallel and arranged either side of a media transport path in the self-service terminal, such that the media passes between the first and the second electrodes.

The impedance measuring circuit may comprise: a transimpedance amplifier connected to the second electrode; and a mixer arranged to mix an output of the transimpedance amplifier and a phase shifted version of the reference signal.

The sensing mechanism may further comprise: a processor arranged to analyze an output of the mixer.

The processor may be further arranged to: determine a quantity of media passing the electrodes from analysis of the output of the mixer.

The phase shifted version of the reference signal may be shifted by 90° with respect to the reference signal.

Each electrode may be separated from the media by an insulating layer. The insulating layer may be provided as a coating on the electrode. The insulating layer may be provided by a support structure that is used to couple the sensing mechanism to the self-service terminal.

The media may comprise at least one bank note and the self-service terminal may comprise an automated teller machine.

The frequency of the modulated signal may be selected to mitigate any effects of moisture in the impedance measuring circuit.

The frequency of the modulated signal may be adjustable.

Many of the attendant features will be more readily appreciated as the same becomes better understood by reference to the following detailed description considered in connection with the accompanying drawings. The preferred features may be combined as appropriate, as would be apparent to a skilled person, and may be combined with any of the aspects of the invention.

BRIEF DESCRIPTION OF THE DRAWINGS

Embodiments of the invention will be described, by way of example, with reference to the following drawings, in which.

Common reference numerals are used throughout the figures to indicate similar features.

DETAILED DESCRIPTION

Embodiments of the present invention are described below by way of example only. These examples represent the best ways of putting the invention into practice that are currently known to the Applicant although they are not the only ways in which this could be achieved.

As described above, double picks in a self-service terminal (SST) are typically detected by passing the media between two rollers and detecting their relative displacement. However, as this is a contact method (i.e. the rollers are in contact with the media), the rollers can impede the movement of the media and may introduce a skew in the media (compared to the transport mechanism) which may later have to be corrected or may require the media to be purged, even if a double pick is not detected. Additionally, many of the known methods can only determine if more than one item has been picked and not exactly how many items have been picked.

Figure 2:
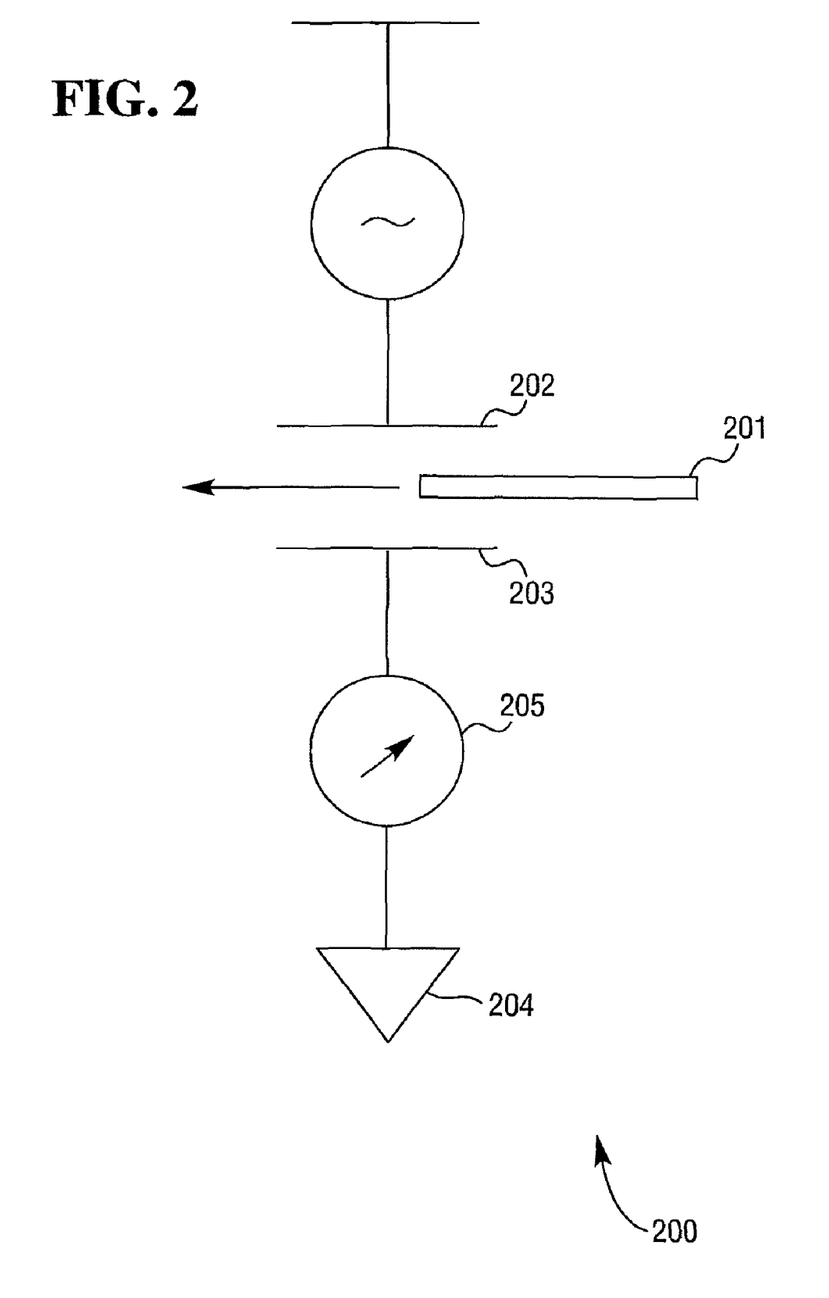
FIG. 2 is a schematic diagram of a non-contact media sensing mechanism.

FIG. 2 is a schematic diagram of a non-contact sensing mechanism which may be used in an SST to characterize the amount of media which is passing by. The item of media 201 passes between two substantially parallel electrodes 202, 203. A modulated signal is applied to one of the electrodes 202 and the signal flowing across the gap to the second electrode 203 to ground 204 is detected 205. This signal which is detected changes as media passes by and from these changes, the amount of media passing by can be characterized.

The sensing mechanism 200 shown in FIG. 2 measures the bulk dielectric properties of the media 201 as it passes between the plates of a capacitor. The sensor does not use a measurement of charge, Q, stored in the capacitor to determine the dielectric properties because belts which are used to carry the media (not shown in FIG. 2) dissipate the charge. Instead, the impedance is measured. If, for example, the modulated signal applied is a sine-wave voltage source, $V(t)=V_0 \sin \omega t$, the current is, for a pure capacitor:

$$I(t)=C\omega V_0 \cos \omega t$$

If only amplitudes are considered (and phases disregarded), the current is:

$$I=V\omega C$$

i.e. if the current is measured, the amplitude of the current is proportional to the capacitance. The capacitance will change dependent on whether there is media between the plates and on the amount of media between the plates. Therefore the detected current can be used to characterize the media passing between the plates.

In reality, the plate arrangement shown in FIG. 2 may not be a pure capacitor and may have a resistive component, in addition to the reactive component of the impedance considered above. However, mechanisms are described below by which only the reactive part of the impedance can be determined. Furthermore, as it is a change in impedance that is being analyzed to characterize the media, detection of a combination of reactive and resistive impedance may simply affect the sensitivity of the measurement.

Figure 3:
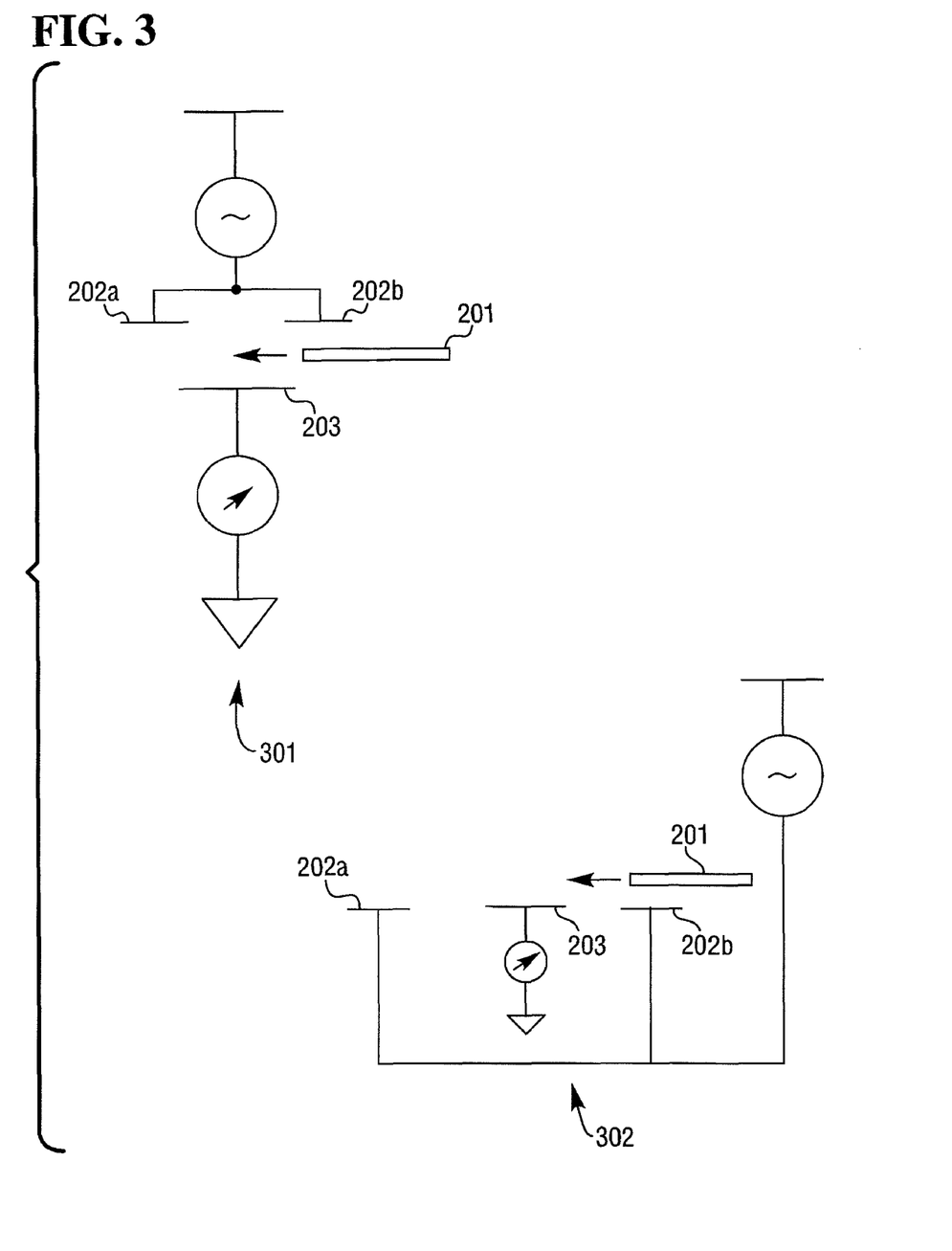
FIG. 3 shows two alternative arrangements of electrodes in a non-contact media sensing mechanism.

FIG. 3 shows two alternative arrangements 301, 302 of electrodes 202a, 202b, 203. As shown in arrangement 302, the media need not pass between the electrodes but may pass over (or even under) the electrodes 202a, 202b, 203. In further embodiments, differential measurement systems may be used.

Figure 4:
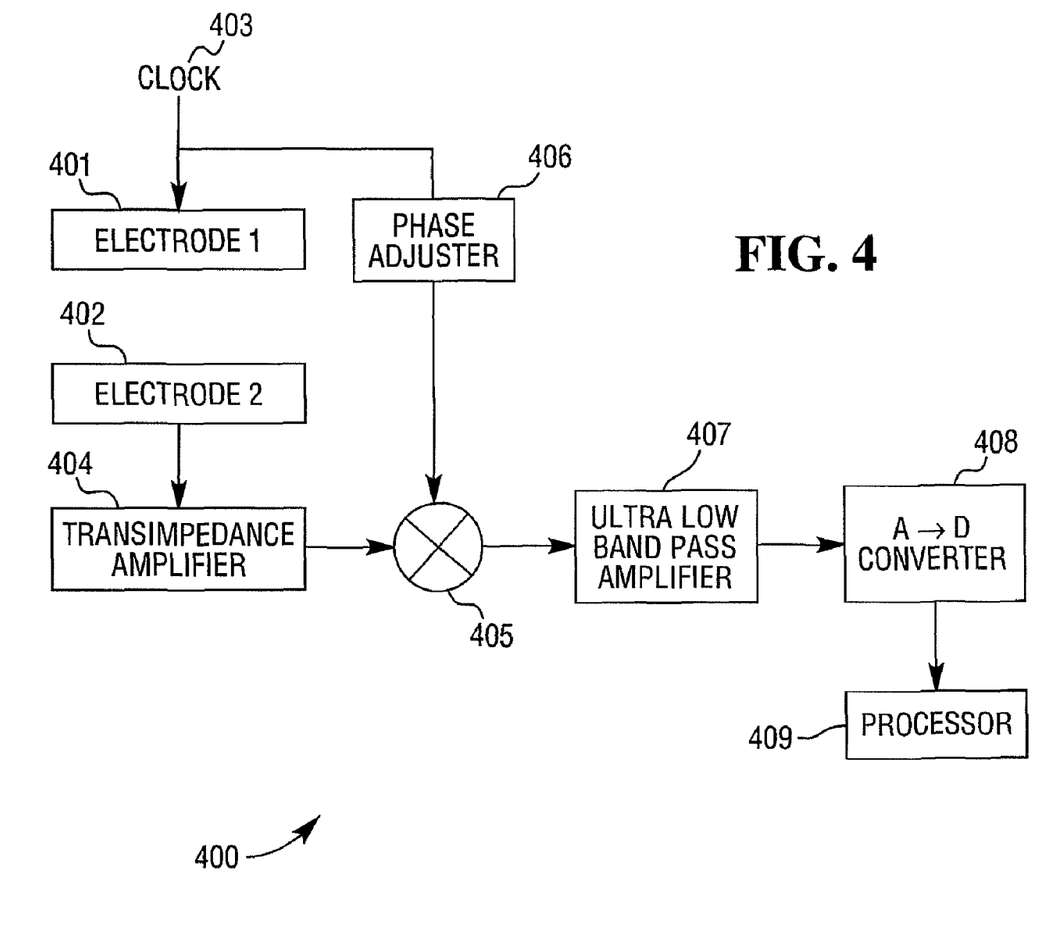
FIG. 4 is a more detailed schematic diagram of a non-contact media sensing mechanism.

FIG. 4 shows a more detailed schematic diagram of a sensing arrangement 400 which comprises two electrodes 401, 402. A clock signal 403 is used to drive one of the electrodes 401. This clock signal may, for example, provide a signal in the range 1-3 MHz, or may operate at a higher frequency (e.g. 13.3 MHz) and the signal may be a square waveform, sine wave or other modulated waveform. The resultant current from the other electrode 402 is converted into a varying voltage using a transimpedance amplifier (TZA) 404. The varying voltage output from the transimpedance amplifier 404 is then mixed (in mixer 405) with the clock signal 403.

Figure 5:
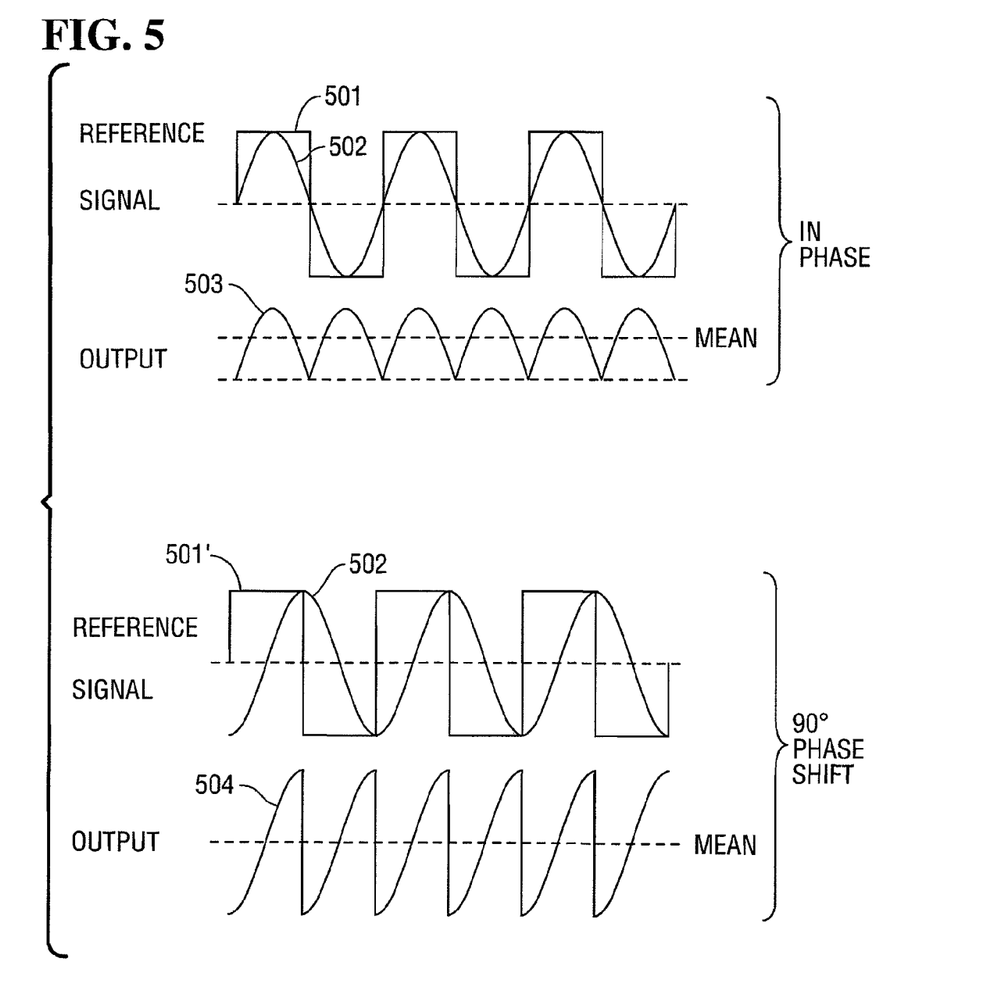
FIGS. 5 and 6 are diagrams showing the operation of the mixer in FIG. 4.
Figure 6:
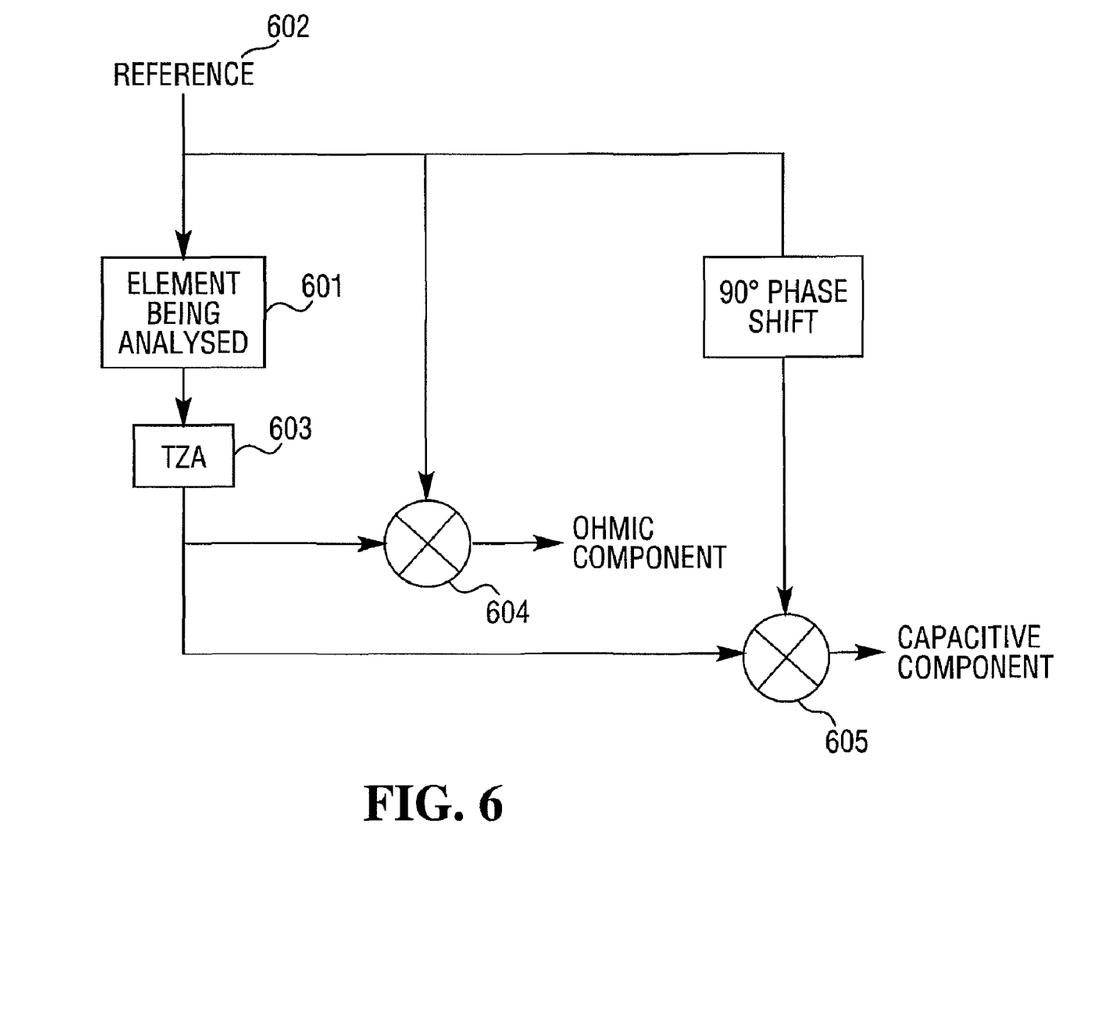

The operation of the mixer can be described with reference to FIGS. 5 and 6. If the reference signal 501 and the signal 502 are in phase, an output 503 is generated which has a positive mean value. However, if the reference signal 501' is shifted by 90°, an output 504 with a mean value of zero is detected. Such a mixer can be used to analyze an element in a circuit, as shown in the schematic diagram of FIG. 6. The element 601 is stimulated using a reference voltage 602, and the output current is detected and converted to a detected voltage signal using a transimpedance amplifier 603. If the element is purely resistive, the detected voltage signal will be in phase with the reference signal and therefore when the two are mixed together (in mixer 604) a positive mean voltage will be detected. This output from the mixing of the reference signal and the detected signal is referred to as the 'ohmic component'. As shown in FIG. 5, if the detected voltage is mixed with a 90° phase shifted version of the reference signal (in mixer 605), a mean voltage of zero will be obtained. However, if element is capacitive, it will introduce a 90° phase shift, with the current leading the voltage by 90°. As a result, if the detected voltage is mixed with the reference signal (in mixer 604), a mean voltage of zero will be obtained whilst mixing the detected voltage with the phase shifted reference (in mixer 605) will result in a non-zero mean voltage. This output from the mixing of the phase shifted reference signal and the detected signal is referred to as the 'capacitive component'.

In the system of FIG. 4, electrodes 401, 402 form a capacitor and therefore introduce a phase shift between the voltage and the current. As a result, the voltage signal output by the transimpedance amplifier will be 90° out of phase with the reference signal. In order to measure the capacitive component, a phase shift is introduced into the reference signal using phase adjuster 406. Whilst introducing a 90° phase shift will result in increased sensitivity of the system, a different value of phase shift could be selected. In an example implementation, the phase shifter 406 may be implemented within a microprocessor.

The output of the mixer 405 is fed into an ultra low band pass amplifier 407 which produces a (substantially) DC voltage which is then converted into a digital signal using an analogue to digital (A to D) converter 408 and input to a processor 409.

The impedance of the item of media may be sampled once for each pick operation or alternatively, multiple sample measurements may be taken as the item of media passes by the electrodes. Use of multiple samples may enable the processor to distinguish between a multiple pick event (where an item of media comprises multiple individual sheets transported together as a single item) and a sheet of media which is folded over. A single pick event is where an item of media comprises a single sheet (or entity, such as a book of stamps). Generally, a single pick event is intended, although a multiple pick event may occur by accident.

Figure 7:
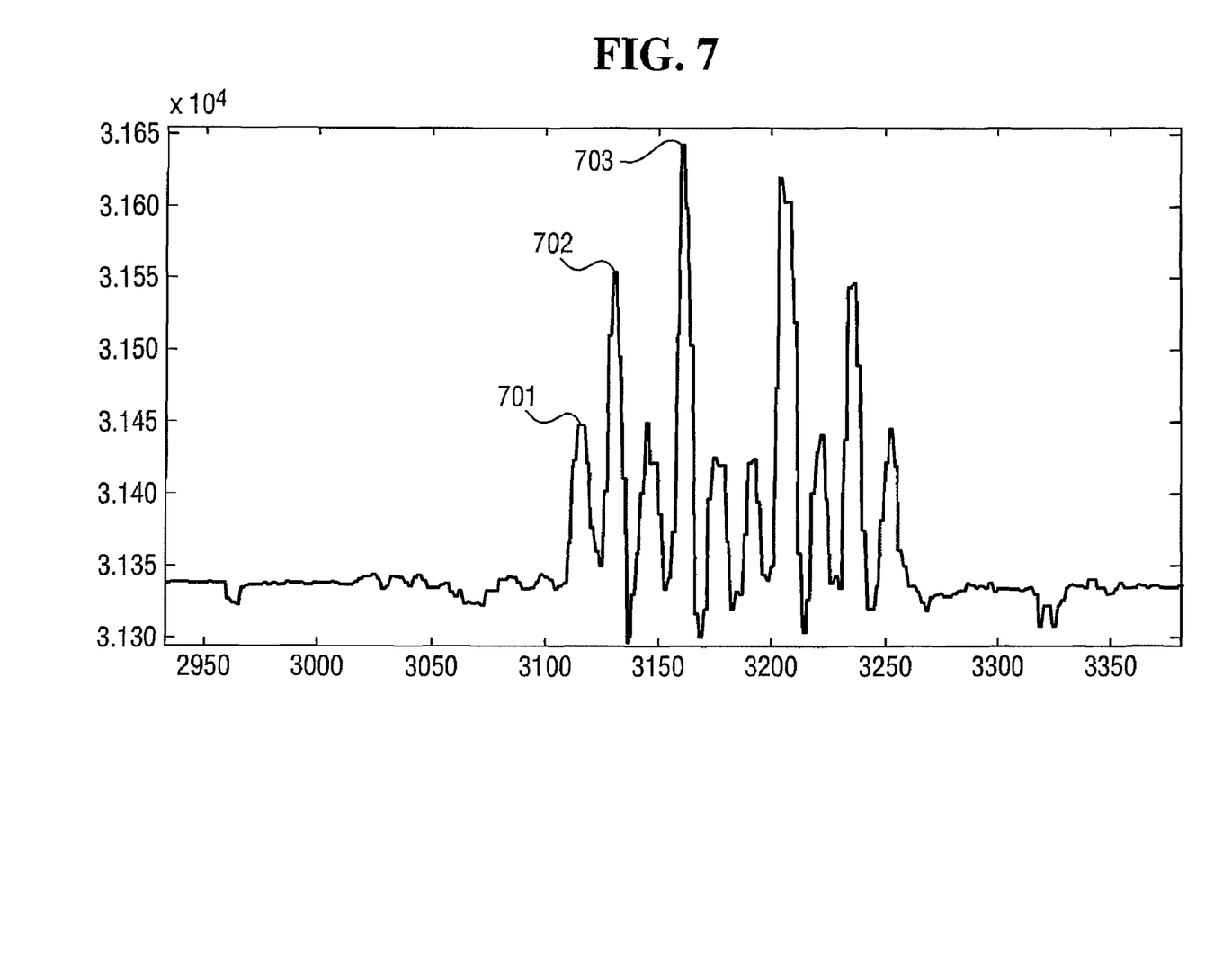
FIGS. 7 and 8 show experimental results using a non-contact media sensing mechanism.

FIG. 7 shows a graph of example results. The trace shows a digital signal, such as that output by the A to D converter 408 in FIG. 4, and shows ten pick operations. The difference between a single pick's peak in the trace 701 and a double pick 702 or triple pick 703 is clearly identifiable. As a result this system may be used to ascertain if the item of media corresponds to a single pick event or a multiple pick event, and also to ascertain for multiple pick events how many sheets are present in the item of media. The results show that the change in dielectric with thickness is approximately linear, at least in the range of thicknesses which are relevant to the use of the system in an SST. This means that in some embodiments, it may be possible to continue to dispense an item of media comprising multiple sheets, rather than rejecting it. As the actual number of sheets picked in each pick operation can be determined, a multiple pick can be detected and characterized (that is, the number of sheets therein counted) so that the correct amount of sheets can be dispensed.

If fewer pieces of media are placed in the purge bin, the purge bin will need to be emptied less frequently and the media cassettes will need to be replenished less frequently. This increases the operational time of the self-service terminal, it also reduces time spent reconciling the contents of the purge bin with multiple pick events, and also increases security by ensuring that fewer sheets (which may be bank notes where the SST is an ATM) are sent to the purge bin.

Figure 8:
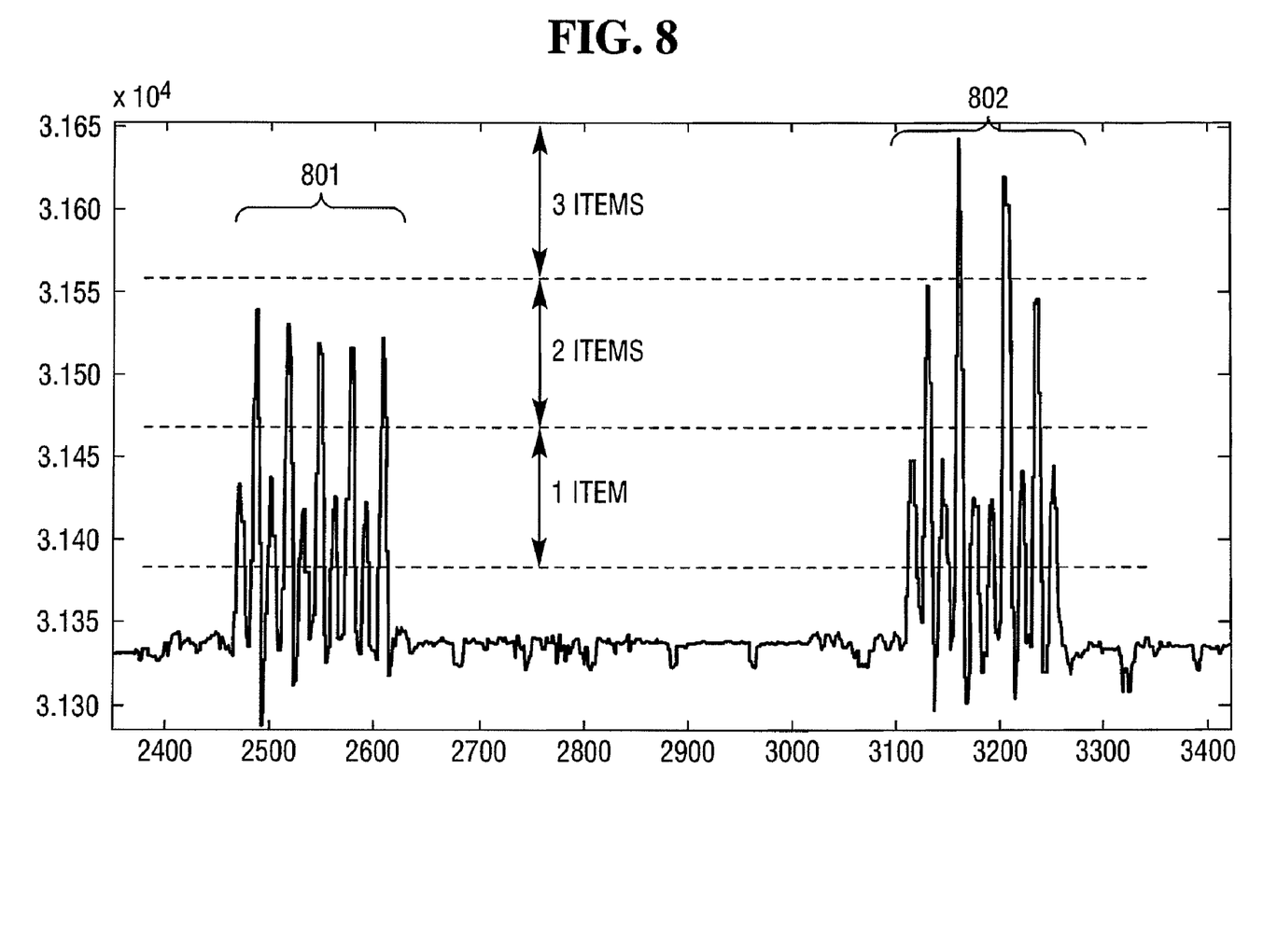

FIG. 8 shows a second graph of example results in which two groups of ten pick operations have been detected. In the first group 801, the pick operations have alternated between single and double picks, whilst in the second group 802, some of the pick operations have picked three pieces of media.

As shown in the experimental results of FIGS. 7 and 8, the level of background impedance may change. This may be affected by temperature, humidity or other parameters. In order to calibrate out such changes, the background impedance level may also be monitored to provide a dynamic baseline from which changes are measured.

The electrodes 401, 402 may be spaced according to the media being picked and detected. In an example, the electrodes may be spaced by up to 5 mm. The spacing may be selected such that if the picked media is folded, the media can still pass through the gap between the electrodes. As also described above, in some embodiments, the media may not pass between electrodes but may pass over the electrodes instead (as shown in FIG. 3), or under the electrodes.

Figure 10:
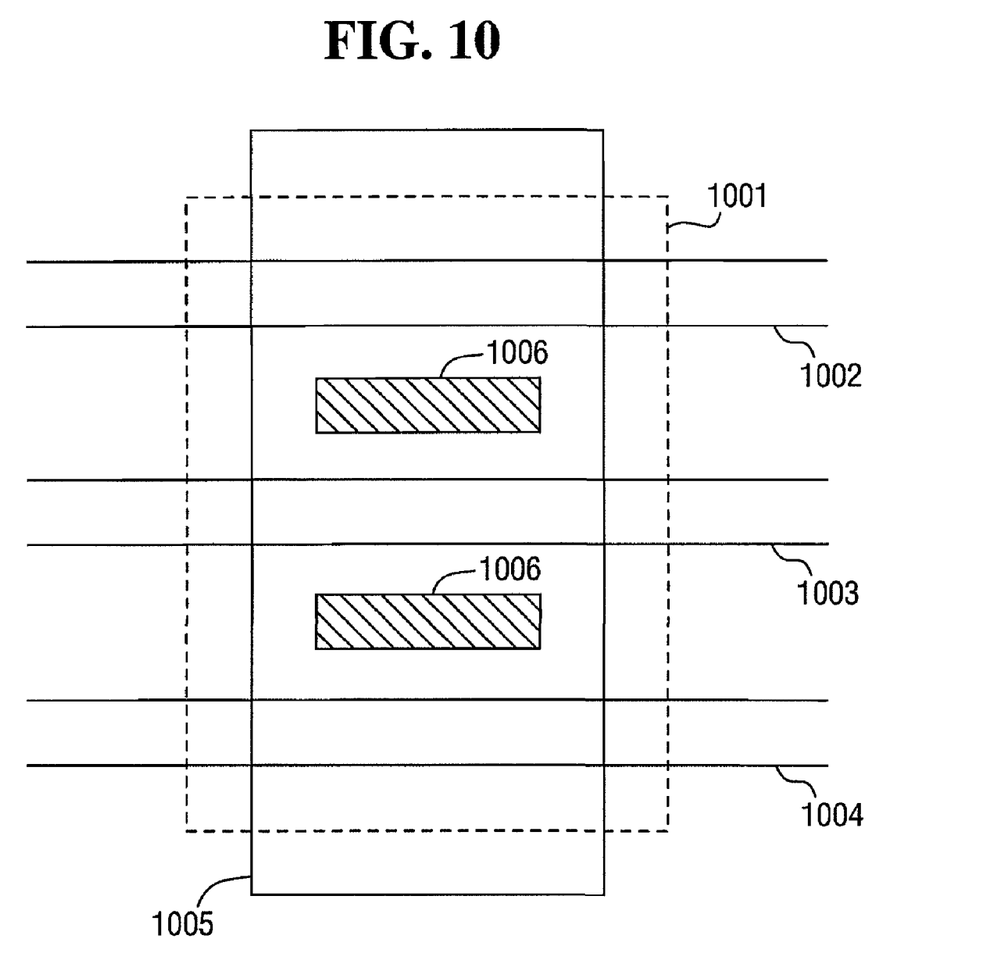
FIGS. 10 and 11 show an example electrode arrangement in a non-contact media sensing mechanism.

Many pieces of media have electrically conductive portions (e.g. a metal strip or foil logo on a bank note), and where such items are to be picked, the media must not come into contact with the electrodes. Therefore in many embodiments, the electrodes are covered with an insulating layer (as shown in FIG. 10 which is described below).

Figure 9:
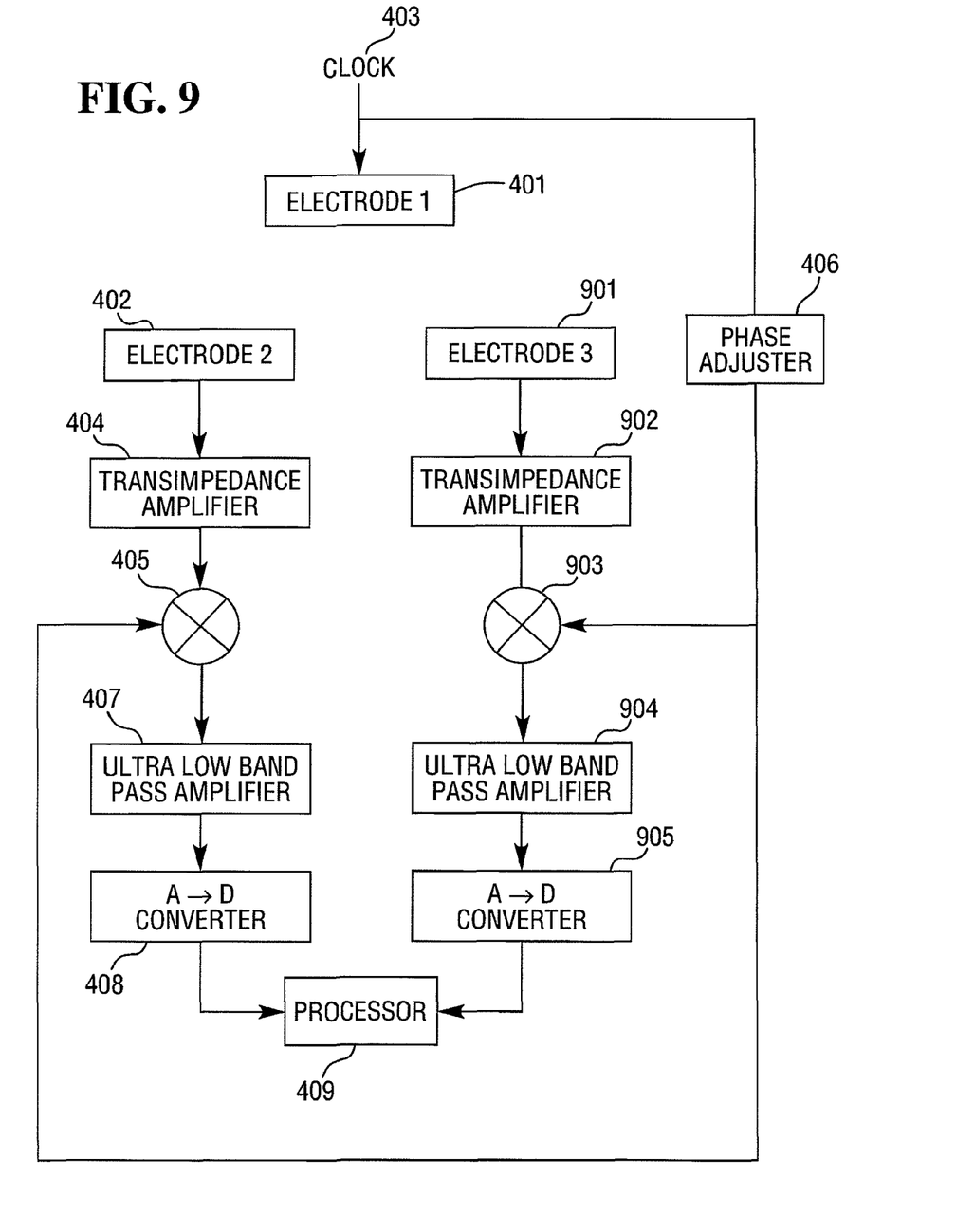
FIG. 9 shows a variation of the sensing mechanism shown in FIG. 4.

In the system shown in FIG. 4, there are only two electrodes; however, as shown in FIG. 3, there may be more than two electrodes. FIG. 9 shows a variation of the system shown in FIG. 4, but with an additional electrode 901 and associated detection and mixing circuitry 902-905. In other examples, there may be more than two lower electrodes 402, 901 and/or there may be more than one upper electrode 401. Whilst the electrodes are referred to as upper/lower, this refers only to the orientation shown in FIGS. 4 and 9. It will be appreciated that the electrodes may be in any suitable orientation and in other examples, the clock signal may be applied to the lower electrode(s) with the detection and mixing circuitry being connected to the upper electrode(s).

The systems shown in FIGS. 4 and 9 may also comprise a reflective optical device which may be used to detect the leading edge of a note. This may be used to trigger the sampling of the impedance or for any other purpose.

An example electrode arrangement can be described with reference to FIGS. 10 and 11 which show a view from above and a cross-sectional view respectively. The media 1001 is held between three pairs of belts 1002-1004 (not shown in FIG. 11) and the electrodes 1006 are mounted in a housing 1005 so that they sit in the gaps between the belts. The housing may have channels in it to accommodate the belts. In this example the electrodes are rectangular with their longer axis parallel to the direction of travel of the media. The electrodes may, for example, be approximately 4 cm long and 1.5 cm wide (or 1.5×0.5 inches). The electrodes may be covered with an insulating layer 1007 (not shown in FIG. 10). The housing of the electrodes 1005 (or the electrodes themselves) may have a shaped edge 1008 to facilitate entry of the notes. In this example, either the top electrodes or the bottom electrodes may receive a common stimulus from the clock (e.g. clock 403) and the other electrode of each pair may be used for detection, as described above.

Figure 11:
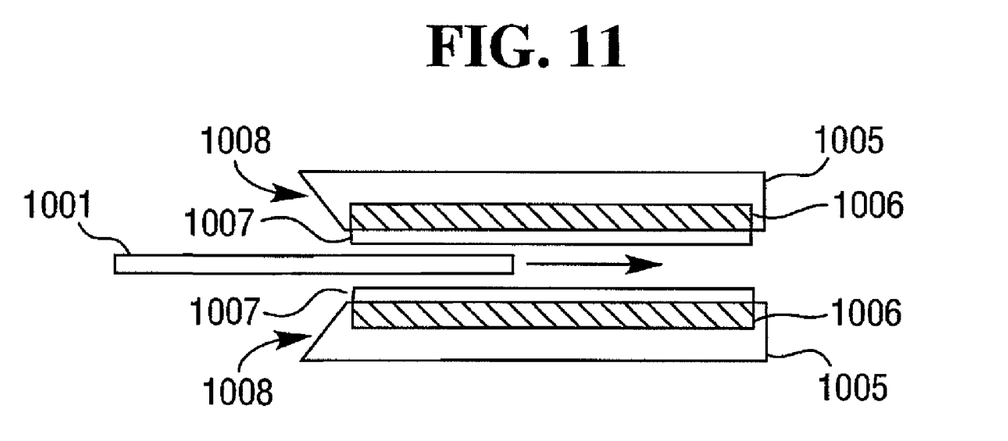

By arranging the electrodes either side of the central belt, as shown in FIGS. 10 and 11, the mechanism can detect and characterize the media irrespective of the size of the media (e.g. in some currencies, bank notes of different denominations are different sizes). Also the ability to make the measurement and characterization is not dependent on the exact position of the media, which might be the case if the electrodes were aligned with the edges of the media. Additionally, if there is already some skew in the item of media, (i.e. such that they are not being transported with all of their edges either parallel or perpendicular to the direction of motion of the belts as shown in FIG. 10), the detection and characterization can also still occur.

It will be appreciated that the arrangement shown in FIGS. 10 and 11 is just one possible arrangement and many other arrangements may be used. In an example, the electrodes may be rectangular but may be arranged with their long axis at right angles to the direction of travel of the media.

In a further example, the media may not be held between belts as it passes the electrodes. Instead, the media may be fed between the electrodes using an alternative transport mechanism, such as pairs of rollers, a gear train, and/or skid plates. Use of belts is beneficial, however, as the belts guide the media through the transport mechanism.

In addition to detecting the number of sheets of an item of media picked during a pick operation, the system and methods described above may also be able to detect folding of media by the use of a dual (or multiple) channel system (as described above and shown in FIG. 9). Aspects of the condition of the media (e.g. media which have adhesive tape holding them together) may also be detected. Whilst the condition of media which is being dispensed by an SST may be controlled by the operator of the SST or the organization that fills the media cassettes, such a technique may also be applied to assessment of media which is being received from a customer in an SST (e.g. an SST with a recycler module which can accept media, verify it and place it into a media cassette or hopper for subsequent dispensing to another customer). If a poor quality or folded piece of media is detected, the recycler may reject the deposited media and return it to the customer making the deposit.

The systems and methods may also be able to detect foreign objects that may be deposited with (or instead of) media. Metallic objects, such as coins and paperclips, and non-metallic objects, such as elastic bands, may be detected. If a foreign object is detected, the recycler (or other deposit mechanism) may reject the foreign object and return it to the customer making the deposit. Any deposited media may still be accepted or may also be rejected and returned to the customer.

The systems and methods described above may also be used in an SST which accepts deposits to confirm that the number of items deposited corresponds to that expected. For example, the methods may be used to determine the number of cheques which are received as a bunch deposit.

The media detection and characterization methods are non-contact methods. This is advantageous because the motion of the media within the SST is not impeded and the detection process cannot introduce skew into the notes. Additionally, as there are no moving parts the mechanism is lower cost and more robust.

The methods described above do not require the media to be parallel to the surfaces of the electrodes. If the media is closer to one electrode than the other, this will not affect the result. The methods and system described above are therefore tolerant to the way in which the media is transported and the way in which the media passes the electrodes.

As described above, the clock signal used to stimulate one of the electrodes may be in the range of 1-3 MHz or may be higher frequency (e.g. 13.3 MHz). Use of lower frequencies (e.g. in the 1-3 MHz range) may be beneficial as there are fewer resulting RF emission problems. If there is moisture on the media, this does not significantly affect the values received. However, if there is excessive moisture, or in some other circumstances, it may be beneficial to use a higher frequency.

Where different types of media are picked from different media cassettes, such as different denominations or currencies of bank notes, train tickets, mobile telephone top-up cards, the dielectric properties of the different types may be different. Where this occurs, the detection and characterization system (e.g. in processor 409) may need to correlate the levels detected with the expected media type. For example, different ranges of detected values may be specified for different media, in a corresponding manner to the ranges shown in FIG. 8 for a particular type of media.

The media detection and characterization system and methods described above can operate with any type of media including, but not limited to, polymer media, optically transparent media (or media which has transparent windows in it), bank notes with metal strips, electrically conductive media etc. The SST may be any kind of SST, including but not limited to, an ATM.

Any range or device value given herein may be extended or altered without losing the effect sought, as will be apparent to the skilled person. It will be understood that the benefits and advantages described above may relate to one embodiment or may relate to several embodiments The term 'comprising' is used herein to mean including the method blocks or elements identified, but that such blocks or elements do not comprise an exclusive list and a method or apparatus may contain additional blocks or elements.

It will be understood that the above description of a preferred embodiment is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention.

The methods described herein may be performed by software in machine readable form on a tangible storage medium. The software can be suitable for execution on a parallel processor or a serial processor such that the method steps may be carried out in any suitable order, or simultaneously. This acknowledges that software can be a valuable, separately tradable commodity. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program.

Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought.

What is claimed is:

1. A method of operating an automated teller machine (ATM) to determine an actual number of sheets of banknotes contained in a currency item, the method comprising:
    passing the currency item across a first electrode and a second electrode;
    measuring an impedance across the first and second electrodes;
    analyzing the measured impedance to detect the currency item;
    wherein measuring the impedance comprises: stimulating the first electrode with a reference modulated voltage signal; and measuring a current from the second electrode;
    wherein measuring a current from the second electrode comprises: converting the current from the second electrode into a varying voltage signal; and mixing the varying voltage signal with a phase shifted version of the reference modulated voltage signal to create an output voltage signal; and
    wherein analyzing the measured impedance to detect the currency item comprises: analyzing the output voltage signal to determine the actual number of sheets of banknotes contained in the currency item.

2. The method according to claim 1, wherein the impedance comprises a reactive component of impedance.

3. A method of operating an automated teller machine (ATM) to determine an actual quantity of sheets of banknotes contained in a currency item, the method comprising:
    passing the currency item across a first electrode and a second electrode;
    measuring an impedance across the first and second electrodes;
    analyzing the measured impedance to detect the currency item;
    wherein analyzing the measured impedance to detect the currency item comprises: analyzing the measured impedance to determine the actual quantity of sheets of banknotes contained in the currency item.

4. The method according to claim 3, wherein analyzing the measured impedance to determine the actual quantity of sheets of banknotes contained in the currency item comprises: comparing the measured impedance to a stored value; and determining the actual quantity of sheets of banknotes based on the comparison.

5. An automated teller machine (ATM) having a sheet transport path along which currency in the form of banknotes can be transported, the ATM comprising:
    a currency cassette arranged to store sheets of banknotes;
    a sheet pick mechanism arranged to pick a currency item from the currency cassette;
    a sheet transport mechanism arranged to transport the picked currency item along the sheet transport path;
    first and second electrodes disposed along the sheet transport path;
    an impedance measuring circuit arranged to measure an impedance across the first and second electrodes as the picked currency item is transported along the sheet transport path past the first and second electrodes; and
    a processor arranged to determine a an actual quantity of sheets of banknotes contained in the picked currency item based upon the measured impedance across the first and second electrodes.

6. The ATM according to claim 5, wherein (i) the first electrode is disposed on one side of the sheet transport path, and (ii) the second electrode is disposed on opposite side of the sheet transport path.

7. The ATM according to claim 6, wherein (i) the first electrode has a substantially planar shape and has a major surface which faces the sheet transport path, (ii) the second electrode has a substantially planar shape and has a major surface which faces the sheet transport path and the major surface of the first electrode, and (iii) the major surface of the first electrode and the major surface of the second electrode are substantially parallel to each other.

8. The ATM according to claim 6, wherein (i) the first electrode has a substantially planar shape and has a major surface which faces the sheet transport path, (ii) the second electrode has a substantially planar shape and has a major surface which faces the sheet transport path, and (iii) the major surface of the first electrode and the major surface of the second electrode are substantially parallel to each other.

9. The ATM according to claim 5, wherein the first and second electrodes are disposed on one side of the sheet transport path.

10. The ATM according to claim 9, wherein (i) the first electrode has a substantially planar shape and has a major surface which faces the sheet transport path, (ii) the second electrode has a substantially planar shape and has a major surface which faces the sheet transport path, and (iii) the major surface of the first electrode and the major surface of the second electrode are substantially parallel to each other.

11. The method according to claim 1, wherein analyzing the measured impedance to detect the currency item further comprises: analyzing the output voltage signal to determine if a banknote sheet contained in the currency item is folded over.

12. The method according to claim 3, wherein analyzing the measured impedance to detect the currency item further comprises: analyzing the measured impedance to determine if a banknote sheet contained in the currency item is folded over.

13. The ATM according to claim 5, wherein the processor is further arranged to (ii) determine if a banknote sheet contained in the picked currency item is folded over based upon the measured impedance across the first and second electrodes.

* * * * *